US 8,019,434 B2

(12) United States Patent
Quiles et al.

(10) Patent No.: US 8,019,434 B2
(45) Date of Patent: Sep. 13, 2011

(54) AUTOMATIC POWER CONTROL FOR A RADIO FREQUENCY TRANSCEIVER OF AN IMPLANTABLE DEVICE (75) Inventors: Sylvia Quiles, Edina, MN (US); Scott Vanderlinde, Plymouth, MN (US); Krishna Sridharan, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 109 days.

(21) Appl. No.: 12/435,928

(22) Filed: May 5, 2009

(65) Prior Publication Data
US 2009/0216298 A1 Aug. 27, 2009

Related U.S. Application Data (62) Division of application No. 10/914,496, filed on Aug. 9, 2004, now Pat. No. 7,539,541.

(51) Int. Cl.
*A61N 1/08* (2006.01)

(52) U.S. Cl. .............................. 607/60; 607/32; 128/903

(58) Field of Classification Search ..................... 607/32, 607/60, 30; 128/903
See application file for complete search history.

(56) References Cited

U.S. PATENT DOCUMENTS

| 4,404,972 A | 9/1983 | Gordon et al. |
| 4,441,498 A | 4/1984 | Nordling |
| 4,486,739 A | 12/1984 | Franaszek et al. |
| 4,519,401 A | 5/1985 | Ko et al. |
| 4,542,535 A | 9/1985 | Bates et al. |
| 4,562,841 A | 1/1986 | Brockway et al. |
| 4,731,814 A | 3/1988 | Becker et al. |
| 4,944,299 A | 7/1990 | Silvian |
| 4,987,897 A | 1/1991 | Funke |
| 5,025,808 A | 6/1991 | Hafner |
| 5,287,384 A | 2/1994 | Avery et al. |
| 5,292,343 A | 3/1994 | Blanchette et al. |
| 5,314,453 A | 5/1994 | Jeutter |
| 5,342,408 A | 8/1994 | deCoriolis et al. |
| 5,350,412 A | 9/1994 | Hoegnelid et al. |
| 5,370,666 A | 12/1994 | Lindberg et al. |
| 5,466,246 A | 11/1995 | Silvian |
| 5,476,488 A | 12/1995 | Morgan et al. |
| 5,568,510 A | 10/1996 | Tam |
| 5,579,876 A | 12/1996 | Adrian et al. |

(Continued)

FOREIGN PATENT DOCUMENTS
EP 0607638 A2 7/1994
(Continued)

OTHER PUBLICATIONS

"U.S. Appl. No. 10/914,499 Final Office Action mailed May 12, 2009", 10 pgs.
(Continued)

*Primary Examiner* — Kennedy J Schaetzle
*Assistant Examiner* — Erica Lee
(74) *Attorney, Agent, or Firm* — Schwegman, Lundberg & Woessner, P.A.

(57) ABSTRACT

Power supplied to a particular telemetry system of an implantable device having multiple telemetry systems is managed by a state machine. Power to a transceiver of a device is terminated if the particular telemetry system remains dormant or inactive for a programmable period of time and power to the transceiver is turned on if a particular signal is received by the implantable device.

20 Claims, 2 Drawing Sheets

U.S. PATENT DOCUMENTS

| | | | |
|---|---|---|---|
| 5,593,430 A | 1/1997 | Renger | |
| 5,603,331 A | 2/1997 | Heemels et al. | |
| 5,650,759 A | 7/1997 | Hittman et al. | |
| 5,683,432 A | 11/1997 | Goedeke et al. | |
| 5,733,313 A | 3/1998 | Barreras, Sr. et al. | |
| 5,752,976 A | 5/1998 | Duffin et al. | |
| 5,752,977 A | 5/1998 | Grevious et al. | |
| 5,759,199 A | 6/1998 | Snell et al. | |
| 5,766,232 A | 6/1998 | Grevious et al. | |
| 5,843,139 A | 12/1998 | Goedeke et al. | |
| 5,861,019 A | 1/1999 | Sun et al. | |
| 5,940,384 A | 8/1999 | Carney et al. | |
| 6,009,350 A | 12/1999 | Renken | |
| 6,083,248 A | 7/2000 | Thompson | |
| 6,115,583 A | 9/2000 | Brummer et al. | |
| 6,115,636 A | 9/2000 | Ryan | |
| 6,155,208 A | 12/2000 | Schell et al. | |
| 6,169,925 B1 | 1/2001 | Villaseca et al. | |
| 6,200,265 B1 | 3/2001 | Walsh et al. | |
| 6,223,083 B1 | 4/2001 | Rosar | |
| 6,275,737 B1 | 8/2001 | Mann | |
| 6,329,920 B1 | 12/2001 | Morrison et al. | |
| 6,424,867 B1 | 7/2002 | Snell et al. | |
| 6,427,088 B1 | 7/2002 | Bowman, IV et al. | |
| 6,434,429 B1 | 8/2002 | Kraus et al. | |
| 6,443,891 B1 | 9/2002 | Grevious | |
| 6,456,256 B1 | 9/2002 | Amundson et al. | |
| 6,470,215 B1 | 10/2002 | Kraus et al. | |
| 6,482,154 B1 | 11/2002 | Haubrich et al. | |
| 6,490,487 B1 | 12/2002 | Kraus et al. | |
| 6,535,766 B1 | 3/2003 | Thompson et al. | |
| 6,564,104 B2 | 5/2003 | Nelson et al. | |
| 6,564,105 B2 | 5/2003 | Starkweather et al. | |
| 6,574,509 B1 | 6/2003 | Kraus et al. | |
| 6,574,510 B2 | 6/2003 | Von Arx et al. | |
| 6,585,644 B2 | 7/2003 | Lebel et al. | |
| 6,600,952 B1 | 7/2003 | Snell et al. | |
| 6,614,406 B2 | 9/2003 | Amundson et al. | |
| 6,622,043 B1 | 9/2003 | Kraus et al. | |
| 6,622,050 B2 | 9/2003 | Thompson | |
| 6,648,821 B2 | 11/2003 | Lebel et al. | |
| 6,659,948 B2 | 12/2003 | Lebel et al. | |
| 6,687,546 B2 | 2/2004 | Lebel et al. | |
| 6,708,065 B2 | 3/2004 | Von Arx et al. | |
| 6,741,886 B2 | 5/2004 | Yonce | |
| 6,801,807 B2 | 10/2004 | Abrahamson | |
| 6,868,288 B2 | 3/2005 | Thompson | |
| 6,970,735 B2 | 11/2005 | Uber, III et al. | |
| 6,985,088 B2 | 1/2006 | Goetz et al. | |
| 6,985,773 B2 | 1/2006 | Von Arx et al. | |
| 6,993,393 B2 | 1/2006 | Von Arx et al. | |
| 7,013,178 B2 | 3/2006 | Reinke et al. | |
| 7,107,085 B2 | 9/2006 | Doi | |
| 7,110,823 B2 | 9/2006 | Whitehurst et al. | |
| 7,218,969 B2 | 5/2007 | Vallapureddy et al. | |
| 7,319,903 B2 | 1/2008 | Bange et al. | |
| 7,324,012 B2 | 1/2008 | Mann et al. | |
| 7,359,753 B2 | 4/2008 | Bange et al. | |
| 7,539,541 B2 | 5/2009 | Quiles et al. | |
| 7,738,964 B2 | 6/2010 | Von Arx et al. | |
| 7,881,802 B2 | 2/2011 | Quiles et al. | |
| 2002/0013614 A1 | 1/2002 | Thompson | |
| 2002/0019606 A1 | 2/2002 | Lebel et al. | |
| 2002/0046276 A1 | 4/2002 | Coffey et al. | |
| 2002/0049480 A1 | 4/2002 | Lebel et al. | |
| 2002/0065539 A1 | 5/2002 | Von Arx et al. | |
| 2002/0065540 A1 | 5/2002 | Lebel et al. | |
| 2002/0147388 A1 | 10/2002 | Mass et al. | |
| 2002/0173830 A1* | 11/2002 | Starkweather et al. | 607/60 |
| 2003/0050535 A1 | 3/2003 | Bowman, IV et al. | |
| 2003/0114897 A1 | 6/2003 | Von Arx et al. | |
| 2003/0114898 A1 | 6/2003 | Von Arx et al. | |
| 2003/0135246 A1 | 7/2003 | Mass et al. | |
| 2003/0149459 A1 | 8/2003 | Von Arx et al. | |
| 2003/0174069 A1 | 9/2003 | Goetz et al. | |
| 2003/0216793 A1 | 11/2003 | Karlsson et al. | |
| 2004/0030260 A1 | 2/2004 | Von Arx | |
| 2004/0047434 A1 | 3/2004 | Waltho | |
| 2004/0106967 A1 | 6/2004 | Von Arx et al. | |
| 2004/0260363 A1 | 12/2004 | Arx et al. | |
| 2005/0204134 A1 | 9/2005 | Von Arx et al. | |
| 2005/0240245 A1 | 10/2005 | Bange et al. | |
| 2005/0283208 A1 | 12/2005 | Von Arx et al. | |
| 2005/0288738 A1 | 12/2005 | Bange et al. | |
| 2006/0025834 A1 | 2/2006 | Von Arx et al. | |
| 2006/0029100 A1 | 2/2006 | Dove | |
| 2006/0030901 A1 | 2/2006 | Quiles et al. | |
| 2006/0030902 A1 | 2/2006 | Quiles et al. | |
| 2006/0030903 A1 | 2/2006 | Seeberger et al. | |
| 2006/0116744 A1 | 6/2006 | Von Arx et al. | |
| 2006/0161223 A1 | 7/2006 | Vallapureddy et al. | |
| 2006/0194615 A1 | 8/2006 | Vallapureddy et al. | |
| 2007/0100396 A1 | 5/2007 | Freeberg | |
| 2007/0185550 A1 | 8/2007 | Vallapureddy et al. | |
| 2007/0260293 A1 | 11/2007 | Carpenter et al. | |
| 2008/0055070 A1 | 3/2008 | Bange et al. | |
| 2008/0114412 A1 | 5/2008 | Bange et al. | |
| 2008/0215121 A1 | 9/2008 | Bange et al. | |
| 2008/0288024 A1 | 11/2008 | Abrahamson | |
| 2010/0152816 A1 | 6/2010 | Von Arx et al. | |

FOREIGN PATENT DOCUMENTS

| | | |
|---|---|---|
| EP | 1308184 A2 | 5/2003 |
| EP | 1495783 A1 | 1/2005 |
| WO | WO-99/12302 A1 | 3/1999 |
| WO | WO-03/053515 A1 | 7/2003 |
| WO | WO-2005/099817 A1 | 10/2005 |
| WO | WO-2006/020546 A1 | 2/2006 |
| WO | WO-2006/020549 A1 | 2/2006 |
| WO | WO-2008/027655 A1 | 3/2008 |

OTHER PUBLICATIONS

"U.S. Appl. No. 10/914,499, Response filed Jul. 13, 2009 to Final Office Action mailed May 12, 2009", 10 pgs.

"European Application No. 05783799.9 , Communication pursuant to Article 94(3) EPC mailed on Jun. 16, 2009", 3 pgs.

"European Application No. 05783882.3 , Communication pursuant to Article 94(3) EPC mailed Jun. 16, 2009", 3 pgs.

"U.S. Appl. No. 10/071,255, Response and Preliminary Amendment filed Oct. 20, 2004 to Restriction Requirement mailed Sep. 28, 2004", 7 pgs.

"U.S. Appl. No. 10/071,255, Restriction Requirement mailed Sep. 28, 2004", 5 pgs.

"U.S. Appl. No. 10/071,255, Non Final Office Action mailed Jan. 7, 2005", 6 pgs.

"U.S. Appl. No. 10/071,255, Notice of Allowance mailed Jun. 15, 2005", 4 pgs.

"U.S. Appl. No. 10/071,255, Preliminary Amendment filed Oct. 5, 2005", 12 pgs.

"U.S. Appl. No. 10/071,255, Response filed Apr. 7, 2005 Non-Final Office Action mailed Jan. 7, 2005", 12 pgs.

"U.S. Appl. No. 10/914,496, Final Office Action mailed May 23, 2007", 11 pgs.

"U.S. Appl. No. 10/914,496, Final Office Action mailed Sep. 22, 2008", 12 pgs.

"U.S. Appl. No. 10/914,496, Non Final Office Action mailed Dec. 5, 2006", 9 pgs.

"U.S. Appl. No. 10/914,496, Non-Final Office Action mailed Mar. 18, 2008", 9 pgs.

"U.S. Appl. No. 10/914,496, Notice of Allowance mailed Jan. 16, 2009", 4 pgs.

"U.S. Appl. No. 10/914,496, Response filed Mar. 5, 2007 to Non Final office Action mailed Dec. 5, 2006", 12 pgs.

"U.S. Appl. No. 10/914,496, Response filed Jun. 18, 2008 to Non-Final Office Action mailed Mar. 18, 2008", 10 pgs.

"U.S. Appl. No. 10/914,496, Response filed Aug. 22, 2007 to Final Office Action mailed May 23, 2007", 12 pgs.

"U.S. Appl. No. 10/914,496, Response filed Nov. 24, 2008 to Final Office Action mailed Sep. 22, 2008", 9 pgs.

"U.S. Appl. No. 10/914,496, Response filed Dec. 12, 2007 to Restriction Requirement mailed Nov. 13, 2007", 7 pgs.

"U.S. Appl. No. 10/914,496, Restriction Requirement mailed Nov. 13, 2007", 5 pgs.

"U.S. Appl. No. 10/914,499, Non-Final Office Action mailed May 29, 2007", 11 pgs.

"U.S. Appl. No. 10/914,499, Final Office Action mailed Jan. 24, 2008", 10 pgs.

"U.S. Appl. No. 10/914,499, Non-Final Office Action mailed Apr. 24, 2008", 5 pgs.

"U.S. Appl. No. 10/914,499, Non-Final Office Action mailed on Nov. 5, 2008", 12 pgs.

"U.S. Appl. No. 10/914,499, Response filed Feb. 5, 2009 to Non-Final Office Action mailed Nov. 5, 2008", 12 pgs.

"U.S. Appl. No. 10/914,499, Response filed Apr. 14, 2008 to Final Office Action mailed Jan. 24, 2008", 11 pgs.

"U.S. Appl. No. 10/914,499, Response filed Jun. 30, 2008 to Non-Final Office Action mailed Apr. 24, 2008", 10 pgs.

"U.S. Appl. No. 10/914,499, Response filed Oct. 23, 2007 to Non-Final Office Action mailed May 29, 2007", 11 pgs.

"U.S. Appl. No. 10/914,638, Final Office Action mailed Apr. 17, 2007", 9 pgs.

"U.S. Appl. No. 10/914,638, Notice of Allowance mailed Mar. 21, 2008", 4 pgs.

"U.S. Appl. No. 10/914,638, Notice of Allowance mailed Oct. 22, 2007", 4 pgs.

"U.S. Appl. No. 10/914,638, Response filed Jan. 18, 2007 to Non-Final Office Action mailed Oct. 18, 2006", 16 pgs.

"U.S. Appl. No. 10/914,638, Response filed Aug. 17, 2007 to Final Office Action mailed Apr. 17, 2007", 8 pgs.

"U.S. Appl. No. 10/914,638, Non-Final Office Action mailed Oct. 18, 2006", 9 pgs.

"U.S. Appl. No. 11/101,142, Notice of Allowance mailed Nov. 27, 2007", 6 pgs.

"U.S. Appl. No. 11/101,142, Non-Final Office Action mailed Jun. 20, 2007", 7 pgs.

"U.S. Appl. No. 11/101,142, Response filed Sep. 20, 2007 to Non-Final Office Action mailed Jun. 20, 2007", 7 pgs.

"U.S. Appl. No. 11/244,273, Restriction Requirement mailed Jul. 22, 2008", 10 pgs.

"U.S. Appl. No. 11/244,273, Response filed Mar. 2, 2009 to Non-Final Office Action mailed Nov. 28, 2008", 13 pgs.

"U.S. Appl. No. 11/244,273, Non-Final Office Action mailed on Nov. 28, 2008", 7 pgs.

"U.S. Appl. No. 11/244,273, Response filed Oct. 22, 2008 to Restriction Requirement mailed Jul. 22, 2008", 13 pgs.

"International Application No. PCT/US03/03748, International Search Report mailed Oct. 20, 2003", 5 pgs.

"International Application No. PCT/US2005/028052, International Search Report and Written Opinion mailed Nov. 29, 2005", 12 pgs.

"International Application No. PCT/US2005/028059, International Search Report and Written Opinion mailed Jan. 12, 2005", 13 pgs.

"Prosecution File History for U.S. Appl. No. 10/914,496, filed Aug. 9, 2004", 56 pgs.

Prosecution File History for U.S. Appl. No. 10/914,638, filed Aug. 9, 2004, 42 pgs.

Quiles, S., "Telemetry Switchover State Machine With Firmware Priority Control", U.S. Appl. No. 10/914,499, filed Aug. 9, 2004, 30 pgs.

Seeberger, M., "Dynamic Telemetry Link Selection for an Implantable Device", U.S. Appl. No. 10/914,638, filed Aug. 9, 2004, 35 pgs.

"U.S. Appl. No. 10/914,499, Advisory Action mailed Aug. 4, 2009", 5 pgs.

"U.S. Appl. No. 10/914,499, Final Office Action mailed Jul. 20, 2010", 5 pgs.

"U.S. Appl. No. 10/914,499, Non-Final Office Action mailed Feb. 3, 2010", 11 pgs.

"U.S. Appl. No. 10/914,499, Response filed May 3, 2010 to Non Final Office Action mailed Feb. 3, 2010", 12 pgs.

"U.S. Appl. No. 10/914,499, Response filed Aug. 31, 2010 to Final Office Action mailed Jul. 20, 2010", 10 pgs.

"U.S. Appl. No. 10/914,499, Response filed Nov. 10, 2009 to Advisory Action mailed Aug. 4, 2009", 12 pgs.

"U.S. Appl. No. 11/325,564, Examiner Interview Summary mailed Jun. 24, 2009", 2 pgs.

"U.S. Appl. No. 11/325,584, Notice of Allowance mailed Mar. 23, 2010", 4 pgs.

"U.S. Appl. No. 11/325,584, Notice of Allowance mailed Oct. 21, 2009", 5 pgs.

"U.S. Appl. No. 12/145,343 Restriction Requirement mailed Aug. 26, 2010", 7 pgs.

"European Application No. 05783799.9, Response filed Oct. 23, 2009 to Communication mailed Jun. 16, 2009", 9 pgs.

"European Application No. 05783882.3, Response filed Oct. 22, 2009 to Communication mailed Jun. 16, 2009", 7 pgs.

"U.S. Appl. No. 10/914,499, Notice of Allowance mailed Sep. 29, 2010", 4 pgs.

"U.S. Appl. No. 12/145,343, Non-Final Office Action mailed Oct. 26, 2010", 10 pgs.

"U.S. Appl. No. 12/145,343, Response filed Sep. 14, 2010 to Restriction Requirement mailed Aug. 26, 2010", 8 pgs.

"European Application Serial No. 05783799.9, Office Action mailed Oct. 25, 2010", 3 pgs.

* cited by examiner

AUTOMATIC POWER CONTROL FOR A RADIO FREQUENCY TRANSCEIVER OF AN IMPLANTABLE DEVICE

CLAIM OF PRIORITY

This application is a Divisional of U.S. application Ser. No. 10/914,496, filed Aug. 9, 2004, now issued as U.S. Pat. No. 7,539,541, which is incorporated herein by reference in its entirety.

CROSS-REFERENCE TO RELATED DOCUMENTS

This document is related to U.S. patent application Ser. No. 10/914,499, entitled "TELEMETRY SWITCHOVER STATE MACHINE WITH FIRMWARE PRIORITY CONTROL," filed Aug. 9, 2004 by Quiles et al. and is incorporated herein by reference.

This document is related to U.S. patent application Ser. No. 10/914,638, entitled "DYNAMIC TELEMETRY LINK SELECTION FOR AN IMPLANTABLE DEVICE," filed Aug. 9, 2004, now issued as U.S. Pat. No. 7,406,349 by Seeberger et al. and is incorporated herein by reference.

This document is related to U.S. patent application Ser. No. 10/025,223, entitled "A TELEMETRY DUTY CYCLE MANAGEMENT SYSTEM FOR AN IMPLANTABLE MEDICAL DEVICE," filed Dec. 19, 2001, now issued as U.S. Pat. No. 6,993,393 by Von Arx et al. and is incorporated herein by reference.

TECHNICAL FIELD

This document pertains generally to implantable devices, and more particularly, but not by way of limitation, to automatic power control for a radio frequency transceiver of an implantable device.

BACKGROUND

Implantable devices are typically powered by a life-limited battery. Inductive telemetry systems for implantable devices draw relatively low current and thus, enjoy wide popularity. Inductive telemetry systems, however, have a limited communication range and are recognized as inconvenient and relatively slow.

Radio frequency telemetry systems offer greater bandwidth but at the cost of increased current consumption. For example, monitoring for an incoming far field radio frequency signal can draw as much power as transmitting a signal using an inductive telemetry system.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed herein.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The examples may be combined, other examples may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Introduction

Providing electrical power to a far field radio frequency transceiver when the likelihood of receiving a radio frequency signal is low or not possible is wasteful of energy resources. In one example, the present system provides methods and systems for managing power delivered to a far field radio frequency transceiver of an implantable device. As used herein, the phrase radio frequency refers to communications conducted using far field radiation and reception. Far field refers to distances greater than or equal to $\lambda/2\pi$ where $\lambda$ is the wavelength. In general, the frequencies used for radio frequency telemetry differ from those used with inductive telemetry. Inductive telemetry is conducted using near field radiation and reception where the near field includes distances less than $\lambda/2\pi$.

An implantable device includes multiple telemetry systems to allow exchange of data with a remote device using communication channels having different characteristics. For example, an inductive telemetry system differs from a far field radio frequency telemetry system in terms of bandwidth, communication range and power consumption, security and other factors.

At the outset of a communication session with an implantable device, all telemetry systems are powered up. All systems are initially activated to allow seamless switching between different telemetry links during the session. For example, security considerations may dictate that an inductive telemetry link is used rather than a far field radio frequency telemetry link. As another example, a far field radio frequency telemetry link may be preferred rather than using a wand associated with an inductive telemetry link for communications conducted during a sterile medical procedure. In addition, reliability considerations may dictate that one telemetry system is used rather than another. Furthermore, the availability of an open communication channel may determine whether communications can be conducted using far field radio frequency telemetry or inductive telemetry.

The implantable device communicates with an external device using a single telemetry link at any given time during a communication session. Electrical power consumed by an unused radio frequency transceiver affects implantable device longevity. In the present system, the radio frequency transceiver is automatically powered down when not in use for an extended period of time and automatically powered up according to programmed parameters. For example, after completing a communication session, the radio frequency transceiver is powered off based on a timing signal without waiting for a shut-down command or completion of a session termination routine. As another example, during a communication session in which interference from other radio frequency transmissions precludes the use of the radio frequency transceiver of the implantable device, power to the transceiver is disabled or extinguished.

In one example, the implantable device includes a processor which executes a program to selectively provide power to one of a plurality of telemetry circuits. If the implantable device does not receive a synchronization signal, or otherwise remains inactive, for a predetermined period of time, then the processor provides a signal to a power controller which disables power to one of the telemetry circuits. For example, after a 100 millisecond period during which the implantable device does not receive a synchronization signal, the power supply to a radio frequency telemetry circuit is disabled. In other example, other metrics for inactivity are used to determine timing for terminating the power supplied to a particular telemetry circuit. For example, inactivity may be associated with a sufficiently low signal quality for a period of time.

After having lost the synchronization signal, a power down timer, or a clock, is started and after expiration of the timer, the power to a particular telemetry circuit is terminated. If communications resumes before expiration of the power down timer, then the timer is canceled. In one example, the duration of the power down timer is programmable.

Structure

Figure 1:
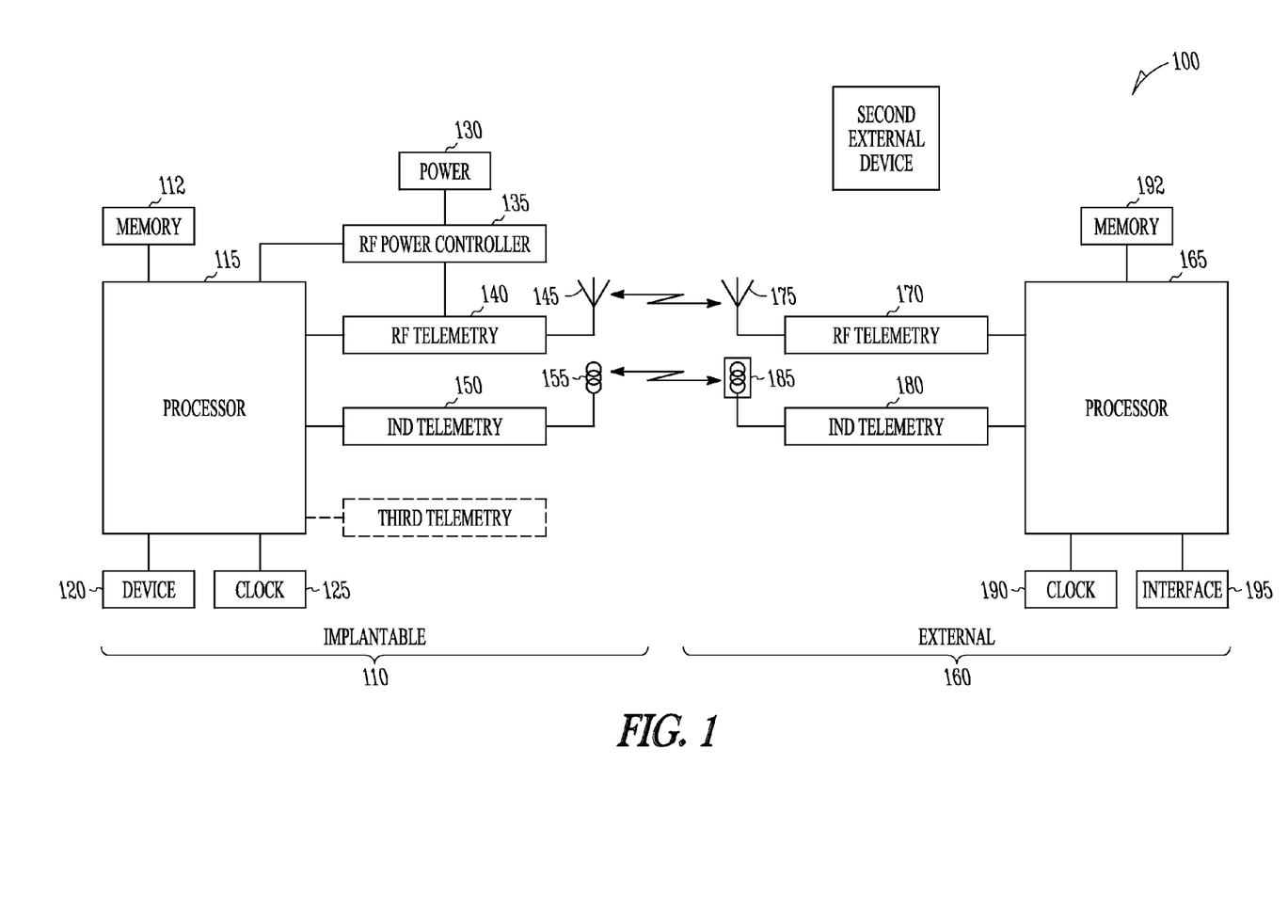
FIG. 1 includes an illustration of an implantable device in communication with an external device.

FIG. 1 illustrates system 100 including implantable device 110 and external device 160, each having dual telemetry circuits.

Implantable device 110 includes processor 115 coupled to device 120. Device 120, in various examples, includes a monitor circuit and a therapy circuit. Exemplary therapy circuits include a pulse generator (such as a pacemaker, a cardiac rhythm therapy device, a heart failure or cardiac resynchronization device, a cardioverter/defibrillator, a pacer/defibrillator) and a drug delivery device (such as an implantable drug pump). In addition, processor 115 is coupled to radio frequency telemetry circuit 140 and inductive telemetry circuit 150. Radio frequency telemetry circuit 140 includes a transceiver coupled to radio frequency antenna 145. Antenna 145 is configured to generate and receive far field signals. Power 130 is delivered to radio frequency telemetry circuit 140 by power controller 135 and in one example, includes a battery. Power controller 135 operates on instructions received from processor 115.

Processor 115, in various examples, includes a microprocessor, a state machine, circuitry, logical gates, firmware or other mechanism.

Inductive telemetry circuit 150 is coupled to inductive antenna 155. In one example, inductive telemetry circuit 150 includes a continuously powered transceiver. Antenna 155 is configured for near field transmission and reception, and, in one example, includes a loop antenna.

Implantable device 110 includes clock 125 coupled to processor 115. Clock 125 provides a timing signal for the benefit of processor 115. Memory 122, also coupled to processor 115, provides storage for data, parameters or instructions. In various examples, memory 122 includes read-only memory, random access memory or other storage and in one example, is remotely programmable.

External device 160 includes processor 165 coupled to interface 195. Interface 195, in various examples, includes a display monitor, a printer, a keyboard, a touch-sensitive screen, a cursor control, a speaker, a microphone, a storage device and a network interface device. External device 160, in one example, includes a programmer for use by a physician or other medical personnel at the time of implantation as well as during follow-up visits. As a programmer, external device 160 allows interrogation as well as programming of implantable device 110, and accordingly, includes a user-accessible interface. External device 160, in one example, includes a remote interrogation device (sometimes referred to as a repeater) which allows connecting with a bi-directional communication network such as a local area network (Ethernet), a wide area network (such as the Internet) or telephone lines in a home (plain old telephone service via the public switched telephone network). In addition, processor 165 is coupled to radio frequency telemetry circuit 170 and inductive telemetry circuit 180. Radio frequency telemetry circuit 170 includes a transmitter and receiver (also referred to as a transceiver) coupled to radio frequency antenna 175. Antenna 175, like antenna 145, is configured to generate and receive far field signals. In one example, far field signals are propagated over a range of greater than one foot.

Inductive telemetry circuit 180 includes a transceiver coupled to inductive antenna 185. Antenna 185, in one example, is part of a hand-operable device sometimes referred to as a wand. The wand enables inductive communications over a short range of approximately 6 inches. Antenna 185, like antenna 155, is configured to generate and receive near field signals and, in one example, includes a loop antenna.

External device 160 includes clock 190 coupled to processor 165. Clock 190 provides a timing signal for the benefit of processor 165. Memory 192, also coupled to processor 165, provides storage for data, parameters or instructions. In various examples, memory 192 includes read-only memory, random access memory, removable or non-removable media or other storage and in one example, is programmable.

Processor 165, in various examples, includes a microprocessor, a state machine, circuitry, logical gates, firmware or other mechanism.

Method

Figure 2:
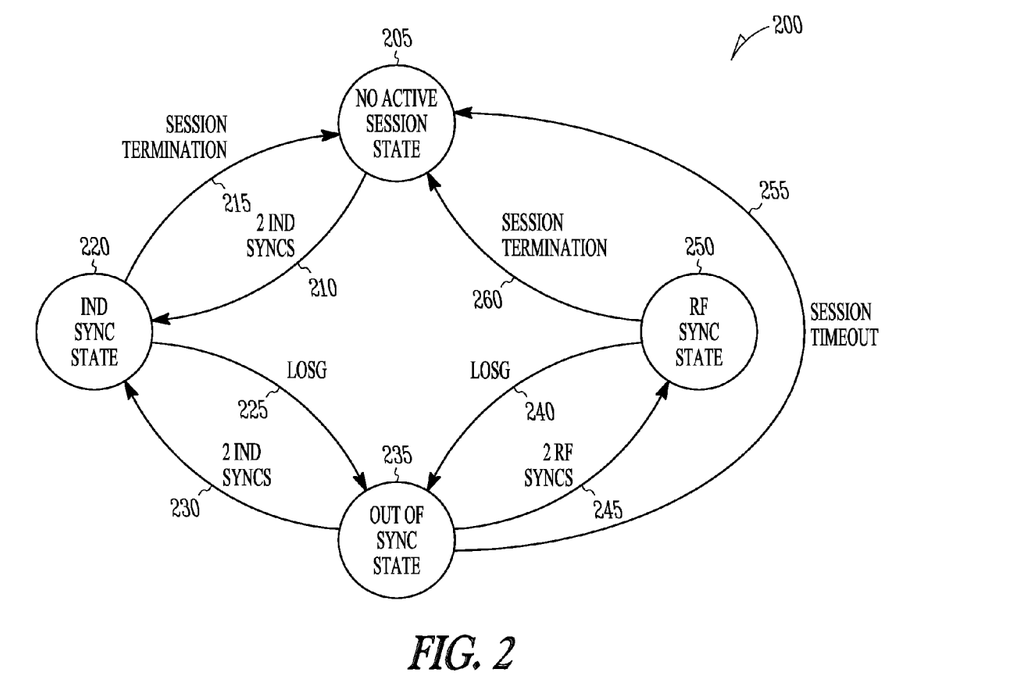
FIG. 2 includes an illustration of a state diagram.

In one example, system 100 operates according to state diagram 200 as shown in FIG. 2. At state 205, state diagram 200 shows an initial condition at a time where implantable device 110 is not actively engaged in a communication session with external device 160. Accordingly, no radio frequency or inductive telemetry link has been established. State 205 is labeled in FIG. 2 as no active session state.

An inductive communication session is established by proceeding along path 210. Inductive telemetry circuit 180 of external device 160 transmits a sequence of synchronization signals (or synchronization frames) generated by processor 165. The sequence of synchronization signals are communicated by a wand (including inductive antenna 185) positioned near inductive antenna 155. In one example, the sequence includes two inductive synchronization signals, as denoted in the figure, however, other signals are also contemplated. A communication session is initiated upon transitioning from state 205 along path 210. In addition to monitoring for two inductive synchronization signals using inductive telemetry 150, implantable device 110 also energizes radio frequency telemetry 140. Electrical current from power 130 is applied to radio frequency telemetry 140 by power controller 135 upon receiving a signal from processor 115.

Upon detecting the inductive synchronization signals, implantable device 110 enters inductive synchronization state 220 during which time implantable device 110 and external device 160 engage in a periodic exchange of data or signals, using inductive telemetry.

If implantable device 110 loses the inductive synchronization signal for a period of time in excess of a particular value, then, as shown by path 225, implantable device 110 drops out of inductive synchronization state 220 and begins to listen concurrently for both an inductive synchronization signal and a radio frequency synchronization signal, at state 235. State 235 is referred to as a stand-by mode in that radio frequency telemetry 140 is powered down after expiration of a power down timer. In one example, radio frequency telemetry 140 is powered up for a period of time following entry into state 235 or at an earlier time. The power down timer is canceled if implantable device 110 transitions out of state 235 prior to expiration.

A physician may cause implantable device 110 to exit state 220 by removing the inductive wand or otherwise terminating the communication session. Path 225 is labeled LOSG to represent the loss of signal associated with the transition from state 220 to state 235. In one example, if implantable device 110 loses the inductive synchronization signal for a period of 100 milliseconds, then implantable device transitions to out of synchronization state 235.

From inductive synchronization state 220, a communication session is terminated by a user entered instruction, as illustrated by path 215. The communication session with one implantable device 110 may be terminated on an instruction received from external device 160, for example, in order to establish a communication session with a different implantable device 110. Session termination, in one example, includes powering off radio frequency telemetry 140 based on a signal from processor 115 provided to power controller 135. Implantable device 110 transitions from inductive synchronization state 220 to no active session state 205 via path 215 upon termination of the communication session.

While at state 235, if implantable device 110 receives two inductive synchronization signals, as shown by path 230, then implantable device 110 returns to state 220. If, on the other hand, implantable device 110 receives two radio frequency synchronization signals, as shown by path 245, then implantable device 110 transitions to radio frequency synchronization state 250. Upon entering radio frequency synchronization state 250, a timing period associated with the stand-by mode is suspended. If implantable device 110 does not receive a synchronization signal (either inductive or radio frequency) for a predetermined period of time, then, as shown by path 255, implantable device 110 treats this as a session time-out and returns to state 205 where no communication session is active. In one example, transitioning along path 255 includes powering down radio frequency telemetry 140. In one example, the predetermined period of time for a session time-out is 5 minutes, however longer or shorter durations are also contemplated.

While at out of synchronization state 235, implantable device 110 concurrently listens, or monitors, for an inductive synchronization signal as well as a radio frequency synchronization signal. In one example, after implantable device 110 has been at state 235 for a period of time, processor 115 provides a signal to power controller 135 to power off radio frequency telemetry 140. In one example, clock 125 provides a timing signal and processor 115 conducts a comparison of the timing signal with a reference value stored in memory 122. In one example, after expiration of a timer, the power to radio frequency telemetry 140 is removed.

While in state 250, implantable device 110 and external device 160 engage in a periodic exchange of data or signals using radio frequency telemetry. If, while in state 250, implantable device 110 loses the radio frequency synchronization signal for a period of time in excess of a particular value, then, as shown by path 240, implantable device 110 drops out of state 250 and concurrently listens for both an inductive synchronization signal or a radio frequency synchronization signal at state 235. A physician may cause implantable device 110 to exit state 250 by terminating the communication session. Path 240 is labeled LOSG to represent the loss of signal associated with the transition from state 250 to state 235. In one example, if implantable device 110 loses the radio frequency synchronization signal for a period of 100 milliseconds, then implantable device transitions to out of synchronization state 235. In one example, the LOSG time period is a programmable value stored in memory 122.

From radio frequency synchronization state 250, a communication session terminated by a user entered instruction, as illustrated by path 260. The communication session with one implantable device 110 may be terminated on an instruction received from external device 160, for example, in order to establish a communication session with a different implantable device 110. Session termination, in one example, includes powering off radio frequency telemetry 140 based on a signal from processor 115 provided to power controller 135. Implantable device 110 transitions from radio frequency synchronization state 250 to no active session state 205 via path 260 upon termination of the communication session.

In one example, system 200 is implemented as a one state automatic stand-by state machine. As such, implantable device 110 is operated in a stand-by mode when operating in out of synchronization state 235. While in stand-by mode, radio frequency telemetry 140 is powered on for a period of time after which power is removed based on a signal provided by processor 115 to power controller 135. In addition, while implantable device 110 is in no active session state 205, radio frequency telemetry 140 is powered off based on a signal provided by processor 115 to power controller 135. Also, while implantable device 110 is in inductive synchronization state 220 or radio frequency synchronization state 250, radio frequency telemetry 140 remains powered on based on a signal provided by processor 115 to power controller 135.

Variations of system 200 are also contemplated. In one example, system 200 can be implemented as a two state automatic stand-by state machine. As such, implantable device 110 is operated in a stand-by mode both when operating in out of synchronization state 235 and when operating in inductive synchronization state 220. While in either state 235 or state 220, radio frequency telemetry 140 is powered on for a period of time after which power is removed based on a signal provided by processor 115 to power controller 135. In addition, and while in state 220, inductive telemetry 150 continues to monitor for inductive synchronization signals. Furthermore, while implantable device 110 is in no active session state 205, radio frequency telemetry 140 is powered off based on a signal provided by processor 115 to power controller 135.

If the radio frequency communication channel is in use by another device or otherwise unavailable, then external device 160 will conduct communications using inductive telemetry 180 and continue to monitor the radio frequency channel for availability. If the inductive link is maintained for more than a predetermined period of time, then radio frequency telemetry 140 of implantable device 110 is powered down and for the duration of the inductive telemetry communication session, radio frequency telemetry 140 remains unpowered. If the inductive synchronization signals are lost (for example, the telemetry wand is removed) while the communication session is active, then radio frequency telemetry 140 is again powered up. In one example, radio frequency telemetry 140 is powered up or powered down based on an instruction received from external device 160.

As a further example, system 200 can be implemented as a three state automatic stand-by state machine. As such, implantable device 110 is operated in a stand-by mode when operating in either out of synchronization state 235, inductive synchronization state 220 or radio frequency synchronization state 250. While operating in either state 235 or state 220, radio frequency telemetry 140 is powered on for a period of time after which power is removed based on a signal provided by processor 115 to power controller 135. Furthermore, while operating in state 250, both inductive telemetry 150 and radio frequency telemetry 140 concurrently monitor for synchronization signals and radio frequency telemetry 140 is powered on for a period of time after which power is removed if no transactions are detected. In one example, the stand-by period of time for state 250 is one hour, however, other periods of time are also contemplated. In addition, and while in state 220, inductive telemetry 150 continues to monitor for inductive synchronization signals and while implantable device 110 is in no active session state 205, radio frequency telemetry 140 is powered off based on a signal provided by processor 115 to power controller 135.

In one example, even while receiving radio frequency synchronization signals, implantable device 110 automatically powers down radio frequency telemetry 140 after a predetermined period of time during which no telemetry transactions are received. In one example, the predetermined period of time is approximately one hour.

Exemplary Alternatives

In one example, the communication link is referred to as half-duplex meaning that only one of implantable device 110 and external device 160 can be transmitting at a time.

External device 160 can send data, commands or instruction to implantable device 110 and also receive responses from implantable device 110. While a session is active, if external device 160 is not sending commands or instructions to implantable device 110, then implantable device 110 is sending internal electrocardiograms and other data from the heart. At a time when external device 160 is not sending commands or instructions, external device 160 is sending out timing pulses and implantable device 110 continues to send data which is displayed or otherwise processed using external device 160. When implantable device 110 is sending data to external device 160, it sends a synchronization pulse interspersed with continuous, real-time data from implantable device 110.

During a communication session, external device 160 periodically sends a timing signal upon which implantable device 110 synchronizes data transmissions. Implantable device 110 continuous to send data while in the synchronized mode. External device 160 receives the continuous stream of data from implantable device 110 and generates a real-time visual display, stores in memory or otherwise processes the data. In order to transmit to implantable device 110, external device 160 briefly interrupts the sequence of timing pulses. Implantable device 110, upon detecting that two synchronization pulses are missing, suspends data transmissions and reverts to a receive mode using the active communication link. In the receive mode, implantable device 110 is receptive to incoming commands, instructions or data from external device 160. In addition, implantable device 110 continues to use the most recent state machine and awaits an indication as to whether the telemetry selection signal has been lost.

In one example, the duration of the radio frequency power down timer is approximately the same as the session time-out timer. In various examples, the radio frequency power down timer is of a shorter or longer duration. In one example, upon detecting an inductive synchronization signal, radio frequency telemetry 140 is powered up.

In one example, processor 115 provides a control signal to power controller 135 based on an instruction received by implantable device 110. In one example, the instruction calls for powering off radio frequency telemetry 140 and as such, the instruction is received by either inductive telemetry 150 or radio frequency telemetry 140 as shown in FIG. 1. In one example, the instruction calls for powering on radio frequency telemetry 140 and as such, the instruction is received by inductive telemetry 150. In one example, upon powering off radio frequency telemetry 140, implantable device 110 enters inductive synchronization state 220 or no active session state 205.

In one example, the synchronization signal is dropped to indicate to implantable device 110 that a command will follow. As noted in FIG. 2, the command can include transitioning from one state to another state.

In one example, the period of time associated with stand-by is two minutes, however, other time periods are also contemplated. For example, while in stand-by mode, if implantable device 110 does not detect a radio frequency synchronization signal within two minutes, then radio frequency telemetry 140 is powered off. After having powered off radio frequency telemetry 140, communications can be re-established by using inductive telemetry 150.

In one example the signal used to control power delivered to a telemetry circuit includes a pair of synchronization signals sent from external device 160. In one example, more or less than two synchronization signals are used to trigger a change in power to a telemetry circuit.

In one example, an instruction, flag or other coded signal is sent by external device 160 to command implantable device 110 to power off or power on a telemetry link.

In one example, implantable device 110 waits for a programmable period of time before determining if a synchronization signal has been lost. The period of time can be programmed by an instruction received from external device 160. In one example, the duration of the loss of signal trigger is determined by a value in a register of memory 122 or otherwise determined through a programmable control. In one example, if a synchronization signal is not received within a predetermined period of time while monitoring for signal using a first telemetry circuit, then the implantable device will revert to a second telemetry circuit. The timing signal, derived from clock 125, determines when the signal has been lost and provides the triggering event to toggle to a different telemetry circuit. The duration of the predetermined period is programmable.

In one example, implantable device 110 waits for a programmable period of time before determining that the communication session has timed out. The period of time can be programmed by an instruction received from external device 160.

In one example, inductive telemetry 150 remains powered at all times and radio frequency telemetry 140 is powered only when it is to be used for communicating and remains unpowered otherwise.

In one example, inductive telemetry circuit 150 is powered or unpowered depending on when it is used for communicating.

In one example, telemetry circuits in addition to, or in lieu of, inductive telemetry and radio frequency telemetry, are contemplated. For example, more than one inductive or radio frequency antenna may be connected to a particular telemetry circuit. In addition, implantable device 110 can include more than one instance of radio frequency telemetry 140, each of which operate using a different carrier frequency or communication protocol. In various examples, different communication channels or telemetry systems (circuits) are used, including an optical channel, an ultrasonic channel and an acoustical channel. In one example, a radio frequency telemetry circuit is powered on or powered off according to a state machine. In one example, a telemetry circuit other than a radio frequency telemetry circuit is powered on or powered off according to a state machine.

In one example, implantable device 110 includes more than two telemetry systems. A state machine for an implantable device 110 having more than two telemetry systems can include more than two states that provide automatic stand-by modes. For example, an implantable device 110 having three telemetry systems can provide an automatic stand-by mode in one, two, three or four states.

In one example, the time period for the loss of signal for radio frequency synchronization is programmable. In various examples, the time period is between 10 and 22,560 milliseconds. In one example, the time period for the loss of signal for inductive synchronization is programmable. In one example, the time period for the loss of signal for inductive synchronization is fixed. In one example, the fixed time period is 100 milliseconds.

In various examples, a loss of a signal provides the trigger to power up or power down radio frequency telemetry 140. In one example, power control is determined by an instruction provided by either implantable device 110 or external device 160.

In one example, more than one communication channel is active simultaneously. The data transmitted on the multiple communication channels, in various examples, is either the same or different. In one example, the data from multiple communication channels is reconciled by an arbitration algorithm or based on other factors such as noise level, bandwidth, reliability and signal quality. Other factors can be evaluated based on error detection/checking routines such as cyclic redundancy code checking or other protocol based mechanisms.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. A method comprising:
   receiving a series of inductive synchronization signals at an implantable device;
   detecting a loss of inductive synchronization signals for a first predetermined period of time and powering a far field radio frequency telemetry circuit of the implantable device in response to detecting the loss of inductive synchronization signals;
   concurrently monitoring for both resumption of an inductive synchronization signal and commencement of a far field radio frequency synchronization signal upon detecting the loss of inductive synchronization signals; and
   terminating power to the far field radio frequency telemetry circuit after a second predetermined period of time if the inductive synchronization signals are not resumed following the detected loss of inductive synchronization signals.

2. The method of claim 1, wherein powering the far field radio frequency telemetry circuit includes powering the far field radio frequency telemetry circuit upon detecting the loss of inductive synchronization signals and subsequent resumption of the inductive synchronization signal.

3. The method of claim 1 further including:
   detecting a series of radio frequency synchronization signals following monitoring; and
   applying power to the far field radio frequency telemetry circuit upon the detecting of the series of radio frequency synchronization signals.

4. The method of claim 3 including monitoring for both resumption of the inductive synchronization signals and commencement of a far field radio frequency synchronization signal upon detecting a loss of the series of radio frequency synchronization signals.

5. The method of claim 4 including declaring termination of a communication session when at least one of the inductive synchronization signals and the series of radio frequency synchronization signals is not resumed.

6. The method of claim 3 further including powering the far field radio frequency telemetry circuit for a third period of time following detecting the series of radio frequency synchronization signals.

7. The method of claim 6 including:
   establishing a far field communication session upon detecting the series of radio frequency synchronization signals; and
   terminating the communication session upon detecting a loss of the series of radio frequency synchronization signals.

8. The method of claim 7, wherein the first predetermined period of time used to detect the loss of the inductive synchronization signals is longer than the period of time used to detect the loss of the series of radio frequency synchronization signals.

9. The method of claim 8 including programming the period of time used to detect the loss of the inductive synchronization signals to be longer than the period of time used to detect the loss of the series of radio frequency synchronization signals.

10. The method of claim 6 including:
    establishing a far field communication session upon detecting the series of radio frequency synchronization signals;
    terminating a far field radio frequency communication session upon receiving a user entered instruction; and removing power from the far field radio frequency telemetry circuit upon termination of the communication session.

11. The method of claim 6 including:
   establishing a far field communication session between the implantable device and a first external device upon detecting the series of radio frequency synchronization signals; and
   conducting communications with the implantable device via an inductive telemetry circuit using a second external device.

12. The method of claim 6 including establishing a far field communication session upon detecting the series of radio frequency synchronization signals, wherein both a near field telemetry circuit and the far field radio frequency telemetry circuit are active simultaneously.

13. The method of claim 1, wherein data is communicated between devices during a communication session by interspersing data between synchronization signals.

14. The method of claim 1 including terminating power to the far field radio frequency telemetry circuit after a second predetermined period of time if the inductive synchronization signals is resumed following the first predetermined period of time.

15. The method of claim 1 including terminating power to the far field radio frequency telemetry circuit after a third predetermined period of time upon failure to detect a series of radio frequency synchronization signals following the first predetermined period of time.

16. The method of claim 1 further including synchronizing the implantable device based on the series of inductive synchronization signals.

17. The method of claim 1, wherein the inductive synchronization signals are received at an inductive antenna separate from a radio frequency antenna.

18. The method of claim 1 including deeming the inductive synchronization signals to be resumed following reception of two of inductive synchronization signals.

19. The method of claim 1 including always powering an inductive telemetry circuit and only powering the radio frequency telemetry circuit upon detecting a loss of the series of inductive synchronization signals.

20. The method of claim 1 including:
   receiving a series of synchronization signals at an implantable device via a third telemetry circuit; and
   powering the far field radio frequency telemetry circuit upon detecting a loss of the series of synchronization signals at the third telemetry circuit.

* * * * *